United States Patent
Weigand et al.

(10) Patent No.: US 9,963,574 B2
(45) Date of Patent: May 8, 2018

(54) PHOTOCHROMIC FLUORENOPYRANS WITH DEFINED DIBENZO[B,D]PYRANO FUSED ATTACHMENT

(71) Applicants: Udo Weigand, München (DE); Yven Rohlfing, München (DE); Herbert Zinner, Rohrbach (DE)

(72) Inventors: Udo Weigand, München (DE); Yven Rohlfing, München (DE); Herbert Zinner, Rohrbach (DE)

(73) Assignee: RODENSTOCK GMBH, München (DE)

( * ) Notice: Subject to any disclaimer, the term of this patent is extended or adjusted under 35 U.S.C. 154(b) by 17 days.

(21) Appl. No.: 14/413,758

(22) PCT Filed: Jul. 11, 2013

(86) PCT No.: PCT/EP2013/002065
§ 371 (c)(1),
(2) Date: Jan. 9, 2015

(87) PCT Pub. No.: WO2014/009020
PCT Pub. Date: Jan. 16, 2014

(65) Prior Publication Data
US 2015/0152246 A1    Jun. 4, 2015

(30) Foreign Application Priority Data
Jul. 12, 2012  (DE) .................. 10 2012 013 748

(51) Int. Cl.
| | | |
|---|---|---|
| C08K 5/1545 | (2006.01) | |
| C07D 493/06 | (2006.01) | |
| C07D 311/94 | (2006.01) | |
| G02B 1/04 | (2006.01) | |
| G02C 7/10 | (2006.01) | |

(52) U.S. Cl.
CPC .......... *C08K 5/1545* (2013.01); *C07D 311/94* (2013.01); *C07D 493/06* (2013.01); *G02B 1/041* (2013.01); *G02C 7/102* (2013.01)

(58) Field of Classification Search
None
See application file for complete search history.

(56) References Cited

U.S. PATENT DOCUMENTS 5,645,767 A    7/1997    Van Gemert
5,698,141 A   12/1997    Kumar

FOREIGN PATENT DOCUMENTS

EP    0912908 A1    5/1999

OTHER PUBLICATIONS

International Search Report and Written Opinion of the International Searching Authority, PCT/EP2013/002065, dated Sep. 11, 2013.

*Primary Examiner* — Robert T Butcher
(74) *Attorney, Agent, or Firm* — McDonald Hopkins LLC

(57) ABSTRACT

The present invention relates to photochromic fluorenopyrans with defined dibenzo[b,d]pyrano fusion in accordance with general formulae (I) or (II) and to their use in plastics of all kinds, particularly for ophthalmic purposes. The photochromic compounds of the invention are distinguished by two pronounced absorption bands of the open form in the visible wavelength range, meaning that with dye molecules of this kind it is possible to replace two conventional photochromic dyes each having only one discrete absorption band. The compounds of the invention, moreover, have a very good lifetime with very high performance.

9 Claims, 2 Drawing Sheets

PHOTOCHROMIC FLUORENOPYRANS WITH DEFINED DIBENZO[B,D]PYRANO FUSED ATTACHMENT

This application is a 35 U.S.C. 371 national stage filing and claims priority to PCT Application PCT/EP2013/002065 entitled "PHOTOCHROMIC FLUORENOPYRANS WITH DEFINED DIBENZO[B,D]PYRANO FUSED ATTACHMENT," filed Jul. 11, 2013, which claims the benefit of German Application 10 2012 013 748.6 entitled "PHOTOCHROMIC FLUORENOPYRANS WITH DEFINED DIBENZO[B,D]PYRANO FUSED ATTACHMENT" filed Jul. 12, 2011, both of which are incorporated by reference herein in their entirety.

The present invention relates to photochromic fluorenopyrans with defined dibenzo[b,d]pyrano fusion in accordance with general formulae (I) or (II) and to their use in plastics of all kinds, particularly for ophthalmic purposes. The photochromic compounds of the invention are distinguished by two pronounced absorption bands of the open form in the visible wavelength range, meaning that with dye molecules of this kind it is possible to replace two conventional photochromic dyes each having only one discrete absorption band. The compounds of the invention, moreover, have a very good lifetime with very high performance.

There have long been known various classes of dye which change color reversibly on irradiation with light of defined wavelengths, especially solar rays. This color change derives from the transition by these dye molecules, in response to light energy, to an excited state ("open form"), which they leave again if the supply of energy is interrupted, reverting to their starting state. These photochromic dyes include various pyran systems, which have already been described in the prior art, with different parent systems and substituents.

Pyrans, especially naphthopyrans and larger ring systems derived from them, are presently the class of photochromic compounds on which there has been the most work. Despite having been first filed as a patent (U.S. Pat. No. 3,567,605) back in 1966, it was not until the 1990s that compounds were developed that appeared suitable for use in eyewear lenses. A suitable class of pyran compounds are, for example, the 2,2-diaryl-2H-naphtho[1,2-b]pyrans or the 3,3-diaryl-3H-naphtho[2,1-b]pyrans, whose open, excited forms exhibit various darkening colors from yellow to red-violet.

2,2-Diaryl-2H-naphtho[1,2-b]pyrans with additional fusion on the pyrano-fused benzene ring are of great interest, since because of their larger ring system they absorb at longer wavelengths, meaning that violet or blue darkening colors are accessible. The fusion involves a substituted benzene ring (in the formula (I) or (II) of the herein-described compounds of the invention, accordingly, the benzene ring having the substituents $R_3$), which is further bridged in ortho-position with the naphthopyran.

If this bridging is produced only via one atom, the result is a five-membered ring fused to the naphthopyran. The use of heteroatoms, more particularly oxygen, as a bridge is described in U.S. Pat. No. 5,651,923 and U.S. Pat. No. 6,018,059. With carbon as bridge atom ("singly indeno-fused naphthopyrans") there exists a series of patent applications (e.g., EP 0 792 468, EP 0 906 366, EP 0 987 260, EP 1 054 010, EP 1 116 723, and EP 1 184 379), differing in particular in the two substituents on the bridge carbon atom. These substituents have a great influence on the lightening rate of the open (excited) form. The open forms of all these photochromic dyes, which may additionally have substituents such as alkyl or alkoxy on the non-indeno-fused benzene ring of the naphthopyran unit, have no double absorption band in the visible wavelength range in each case.

EP 1 674 460 and WO 2011/034202 disclose singly indeno-fused naphthopyrans which additionally have an aryl substituent on the non-indeno-fused benzene ring of the naphthopyran unit.

EP 0 912 908 and EP 0 958 514 disclose indeno-fused naphthopyrans which additionally have a heterocyclic fusion (e.g., benzothiophene, benzofuran, or indole ring system) on the non-indeno-fused benzene ring of the naphthopyran unit. These compounds, however, do not exhibit double absorption character.

If this bridging is generated via two atoms, the result is a fused six-membered ring having diverse possibilities solely for C, O, and N. Compounds with C=O and N—R (lactam bridge) are described in U.S. Pat. No. 6,379,591. Compounds having an unsubstituted $CH_2$—$CH_2$ bridge and also a further fused heterocycle in the 7,8-position of the parent benzopyran are disclosed in U.S. Pat. No. 6,426,023. U.S. Pat. No. 6,506,538 describes the carbocyclic analog compounds in which the H atoms in the bridge may be replaced by OH or $(C_1$-$C_6)$-alkoxy, or two H atoms on a C atom may be replaced by =O. U.S. Pat. No. 6,022,495 describes inter alia compounds having an O—$CR^1R^2$ bridge.

If this connection is generated by three atoms, the result is a fused seven-membered ring having very many possibilities for variation through insertion of heteroatoms. Compounds having a $CH_2$—$CH_2$—$CH_2$ bridge are described in U.S. Pat. No. 6,558,583. Here again, the H atoms in the bridge may be replaced by OH, $(C_1$-$C_6)$-alkyl, or $(C_1$-$C_6)$-alkoxy, or two hydrogen atoms on a C atom may be replaced by =O. For the same substitution pattern, the open form of these photochromic dyes absorbs shorter wavelengths than the fused five-membered and six-membered rings.

The various photochromic dyes available in the prior art, however, have disadvantages which detract substantially from the wear comfort experienced by the eyewear wearer when they are used in sun protection glasses. To start with, the dyes lack sufficiently long wave absorption in both the excited and unexcited states. Moreover, the darkening is frequently subject to excessive temperature sensitivity, and at the same time the lightening may occur too slowly. Furthermore, the dyes available in the prior art often possess an inadequate lifetime and hence permit only little durability of the sun protection glasses. This latter quality becomes perceptible in rapidly declining performance and/or significant yellowing.

A feature common to the above photochromic dyes available in the prior art is that they exhibit only one absorption band of the open form in the visible wavelength range. In order to produce phototropic glasses which darken in neutral colors—that is, in gray or brown shades—there is consequently a need for a trade off among the various photochromic dyes in a mixture in terms of lightening speed, lifetime, and spectral excitation properties, so that the phototropic glass exhibits the same shade at any point during the darkening and lightening cycle. It would therefore be extremely desirable to be able to forgo this trade off.

It is an object of the present invention, accordingly, to provide photochromic dyes with which it is possible to realize phototropic glasses that darken in neutral colors, in other words in gray or brown shades, with only one such photochromic dye. Photochromic dyes of this kind are to be distinguished, furthermore, by the combination of a long wave absorption maximum of the closed form with a steep edge to the visible wavelength range, high darkening performance, very rapid lightening response, and very good light stability.

This object is achieved by the subject matter characterized in the claims.

Provided in particular are photochromic fluorenopyrans with defined dibenzo[b,d]pyrano fusion in accordance with the general formulae (I) or (II):

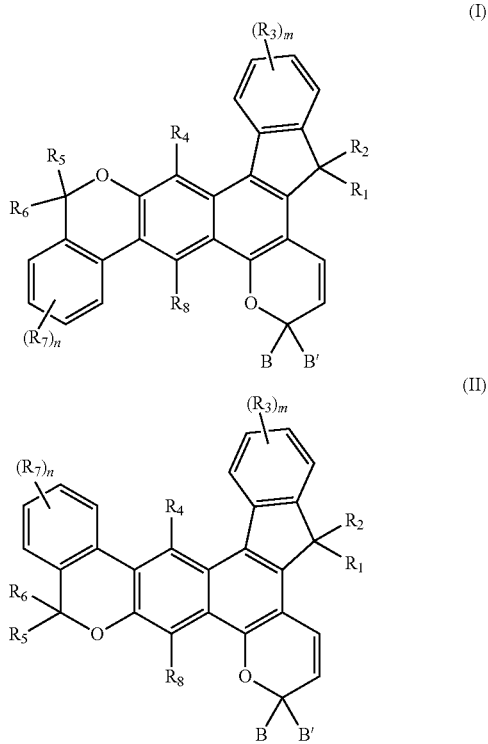

where the radicals $R_1$, $R_2$, $R_3$, $R_4$, $R_5$, $R_6$, $R_7$, and $R_8$ in each case independently of one another are a substituent selected from group α, consisting of a hydrogen atom, a $(C_1-C_6)$-alkyl radical, a $(C_1-C_6)$-thioalkyl radical, a $(C_3-C_7)$-cycloalkyl radical, which may contain one or more heteroatoms, such as O or S, a $(C_1-C_6)$-alkoxy radical, a hydroxyl group, a trifluoromethyl group, bromine, chlorine, fluorine, an unsubstituted or mono- or disubstituted phenyl, phenoxy, benzyl, benzyloxy, naphthyl or naphthoxy radical, the substituents being selectable in turn from group α, preferably from $(C_1-C_6)$-alkyl, $(C_1-C_6)$-alkoxy, bromine, chlorine, or fluorine; m and n independently of one another are an integer from 1 to 4, or the radicals $R_1$ and $R_2$, together with the carbon atom bonded to these radicals, form a 3- to 8-membered, preferably 5- to 7-membered, carbocyclic or heterocyclic (i.e., heterocycles containing oxygen atoms or sulfur atoms) ring which optionally carries one or more, preferably one to four, substituents from group α, it also being possible, however, for one to three aromatic or heteroaromatic ring systems to be fused to this ring, in which case the ring system or systems is or are selected independently of one another from group β, consisting of benzene, naphthalene, phenanthrene, pyridine, quinoline, furan, thiophene, pyrrole, benzofuran, benzothiophene, indole, and carbazole, which may be substituted in turn by one or more substituents selected from group α, and, if two of these substituents carried on the 3- to 8-membered carbocyclic or heterocyclic ring are located on the same ring carbon atom, they may in turn form a 3- to 8-membered carbocyclic or heterocyclic ring, or the radicals $R_5$ and $R_6$, together with the carbon atom bonded to these radicals, form a 3- to 8-membered, preferably 5- to 7-membered, carbocyclic or heterocyclic (i.e., heterocycles containing oxygen atoms or sulfur atoms) ring which optionally carries one or more, preferably one to four, substituents from group α, it also being possible, however, for one to three aromatic or heteroaromatic ring systems to be fused to this ring, in which case the ring system or systems is or are selected independently of one another from group β, consisting of benzene, naphthalene, phenanthrene, pyridine, quinoline, furan, thiophene, pyrrole, benzofuran, benzothiophene, indole, and carbazole, which may be substituted in turn by one or more substituents selected from group α, and, if two of these substituents carried on the 3- to 8-membered carbocyclic or heterocyclic ring are located on the same ring carbon atom, they may in turn form a 3- to 8-membered carbocyclic or heterocyclic ring, or two adjacent radicals $R_3$ form a fused benzene ring, which may be unsubstituted or mono- or disubstituted, in which case the substituents may be selected in turn from group α;

or two adjacent radicals $R_7$ form a fused benzene ring, which may be unsubstituted or mono- or disubstituted, in which case the substituents may be selected in turn from group α;

and B and B' independently of one another are selected from one of the following groups a) or b), where a) are mono-, di-, and trisubstituted aryl radicals, where the aryl radical is phenyl, naphthyl, or phenanthryl;

b) are unsubstituted, mono- and disubstituted heteroaryl radicals, the heteroaryl radical being pyridyl, furanyl, benzofuranyl, thienyl, benzothienyl, 1,2,3,4-tetrahydrocarbazolyl or julolidinyl, the substituents of the aryl or heteroaryl radicals in a) and b) being substituents selected from above-defined group α or group χ, consisting of amino, mono-$(C_1-C_6)$-alkylamino, di-$(C_1-C_6)$-alkylamino, mono- and diphenylamino unsubstituted or mono- or disubstituted on the phenyl ring, piperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, unsubstituted or mono- or disubstituted phenothiazinyl, unsubstituted or mono- or disubstituted phenoxazinyl, unsubstituted or mono- or disubstituted 1,2,3,4-tetrahydroquinolinyl, unsubstituted or mono- or disubstituted 2,3-dihydro-1,4-benzoxazinyl, unsubstituted or mono- or disubstituted 1,2,3,4-tetrahydroisoquinolinyl, unsubstituted or mono- or disubstituted phenazinyl, unsubstituted or mono- or disubstituted carbazolyl, unsubstituted or mono- or disubstituted 1,2,3,4-tetrahydrocarbazolyl and unsubstituted or mono- or disubstituted 10,11-dihydrodibenzo[b,f]azepinyl, it being possible for the substituent or substituents independently of one another to be selected in turn from $(C_1-C_6)$-alkyl, $(C_1-C_6)$-alkoxy, bromine, chlorine, or fluorine;

or where two directly adjacent substituents of the aryl or heteroaryl radicals in a) and b) are a V—$(CR_8R_9)_p$—W moiety, where p is 1, 2 or 3, the radicals $R_8$ and $R_9$ each independently of one another are a substituent selected from group α, and V and W independently of one another may be —O—, —S—, —N$(C_1-C_8)$alkyl, —N$C_6H_5$, —$CH_2$—, —$C(CH_3)_2$—, or —$C(C_8H_5)_2$—, it being possible for two or more adjacent $CR_8R_9$ units of this V—$(CR_8R_9)_p$—W moiety to be part of a benzene ring fused thereto, it being possible for this ring in each case to contain in turn one or more substituents selected from group α, or V and/or W, together with the respectively adjacent $CR_8R_9$ unit, are a fused benzene ring, which may be unsubstituted or mono- or disubstituted, the substituents thereof being selectable from group α.

The molecular structure of the compounds of the invention features a parent fluorene ring system with the substituents $R_1$ to $R_3$. Bonded to one benzene ring of this fluorene is both a dibenzo[b,d] fusion with the substituents $R_4$ to $R_8$, and the photolabile pyran unit with the substituents B and B'. This latter unit is responsible for the photochromic character, since excitation with long wave UVA light causes reversible breaking of the bond between the oxygen of the pyran unit and the carbon atom with the substituents B and B', resulting in a colored merocyanine system being formed.

The compounds of the invention, relative to the photochromic 2H-naphtho[1,2-b]pyrans known in the prior art (U.S. Pat. No. 5,645,767), which do not have any dibenzo[b,d]pyrano fusion, are notable for the fact that they have a double absorption band, i.e., two strong absorption bands, of the open form in the visible wavelength range; cf. FIG. 2.

The first of these two strong absorption bands has an absorption maximum of >500 nm, while the maximum of the second band is in the shorter-wave, visible region (400-500 nm). On account of the latter band, it is possible using the compounds of the invention to omit yellow-darkening or orange-darkening photochromic dyes in neutral-colored phototropic glasses. This is important on the one hand for polymer systems in which these yellow- and orange-darkening dyes—on account of their different molecular structure in comparison to the violet- and blue-darkening dyes that exhibit longer-wave absorption—display inadequate lifetime or introduce other disadvantages. On the other hand it is possible with the photochromic dyes of the invention for the first time to realize phototropic glasses that darken in neutral colors—that is, in gray or brown shades—with only one photochromic dye. Consequently there is no need for the hitherto requisite, laborious process of trade off between the different photochromic dyes in a mixture in terms of lightening rate, lifetime, and spectral excitation properties, so that the phototropic glass has the same shade at each point during the darkening and lightening cycle.

Since, furthermore, the compounds of the invention have high optical clarity (i.e., high transmission in the unexcited state) and also very good light stability, they are eminently suitable for use in phototropic glasses.

Furthermore, the compounds of the invention in the unexcited state are completely colorless (i.e. without esthetically disruptive yellow shade, since the absorption of the closed form is confined to the UV region) and have a very good lifetime.

The present invention is based inter alia on the finding that by means of a precisely defined dibenzo[b,d]pyrano fusion with the substituents $R_4$ to $R_8$ to a fluorenopyran system, it is possible to generate a pronounced double absorption band of the open form in the visible wavelength range. In contrast to the above-described prior art, for the first time in the compounds of the invention, a benzene ring with the substituents $R_7$ is bonded by means of a specific bridge (—O—$CR_5R_6$—) to the photochromic rest of the molecule. This specific bridging according to the invention produces two positive effects: first, it orients the benzene ring with the substituents $R_7$ parallel to the plane of the rest of the molecule, which has the effect of optimum overlapping of the π electrons and hence a correspondingly longer-wave absorption. Secondly, it also provides an additional donor effect (similar to a methoxy group). The combination of these two effects is hitherto undescribed in the prior art, and is responsible for the intensive double absorption bands, shifted toward longer wavelengths, of the open form of the compounds of the invention. On account of this double absorption band in the visible wavelength range, a molecule of the invention of this kind can be used to replace two conventional photochromic dyes—each having one discrete absorption band.

Figure 1:
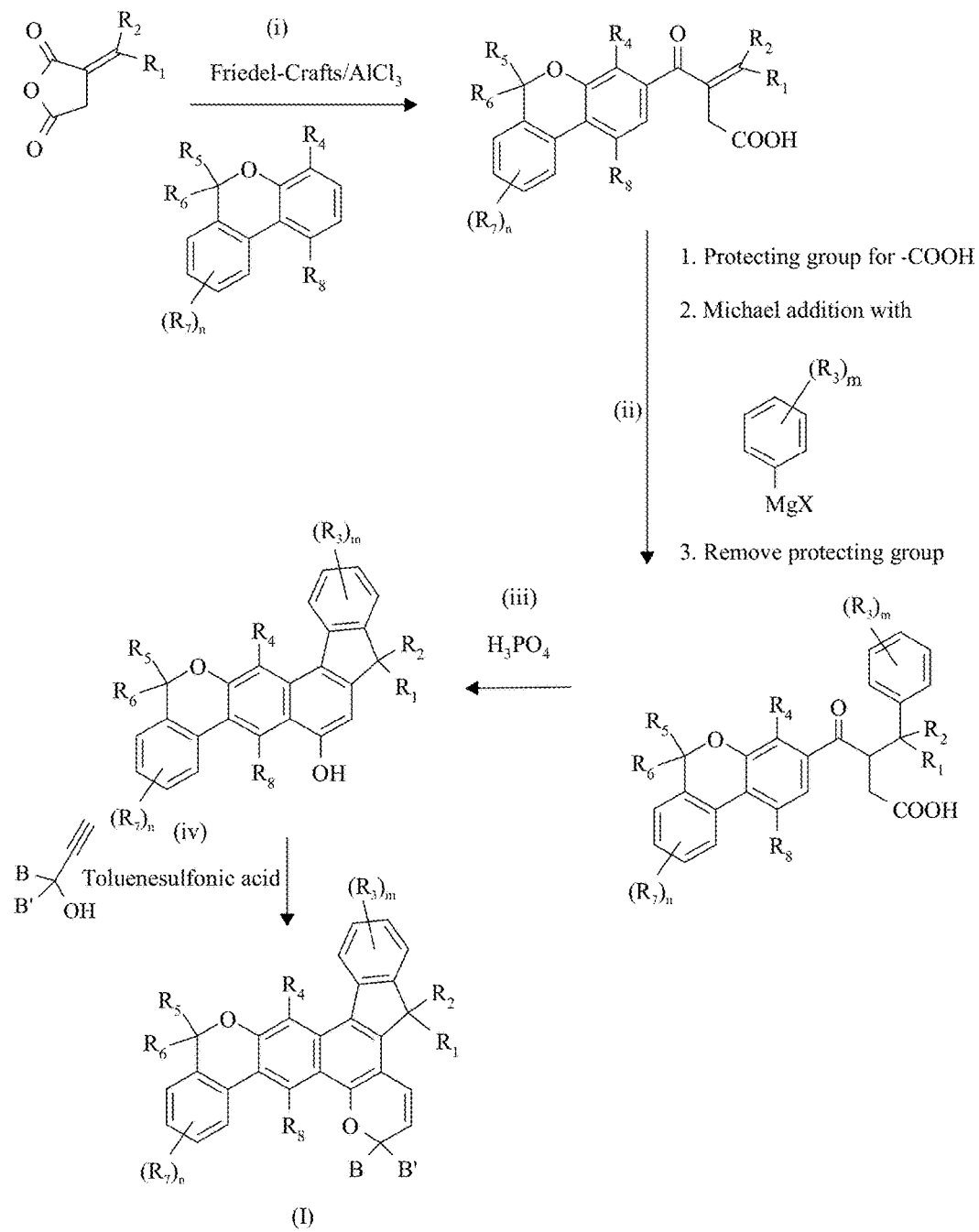
FIG. 1 shows a corresponding synthesis scheme for preparing the inventive compounds in accordance with the above formula (I).

In one embodiment of the present invention, the radicals $R_1$ and $R_2$ are selected independently of one another from a hydrogen atom, a ($C_1$-$C_6$)-alkyl radical or a ($C_3$-$C_7$)-cycloalkyl radical, preferably from a ($C_1$-$C_6$)-alkyl radical or a ($C_3$-$C_7$)-cycloalkyl radical.

In another embodiment of the present invention, the radicals $R_1$ and $R_2$, together with the carbon atom bonded to these radicals, form a 5- to 7-membered carbocyclic or heterocyclic ring which optionally carries one or more substituents from the group α.

In a further embodiment of the present invention, the radicals $R_5$ and $R_6$ are selected independently of one another from a hydrogen atom, a ($C_1$-$C_6$)-alkyl radical or a ($C_3$-$C_7$)-cycloalkyl radical, preferably from a hydrogen atom or a ($C_1$-$C_6$)-alkyl radical.

Preferred photochromic fluorenopyrans with defined dibenzo[b,d]pyrano fusion in accordance with the present invention have the formula (I).

In a further-preferred embodiment of the present invention, the photochromic fluorenopyrans with defined dibenzo[b,d]pyrano fusion have the formula (III) below.

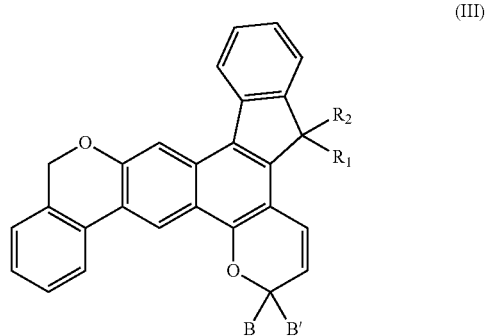

(III)

where the radicals $R_1$, $R_2$, B, and B' are as defined above.

In a further preferred embodiment, the radicals B and B' are selected independently of one another from group a) as defined above.

The substituents of group χ which have nitrogen atoms or carry amine groups are bonded via said atoms or groups to the phenyl, naphthyl or phenanthryl radical of group a).

If, in respect of the substituents of the V—$(CR_8R_9)_p$—W moiety group which may be bonded to the phenyl, naphthyl or phenanthryl radical of group a) for the radicals B and/or B', two or more adjacent carbon atoms of this V—$(CR_8R_9)_p$—W moiety, in each case independently of one another, are part of a benzo ring system fused thereto, this means that in that case the two methylene carbon atoms (—$CH_2$—$CH_2$—) become part of a fused ring system. If, for example, two or three benzo rings are fused, then the structural units present here may then be as follows, for example, as indicated below.

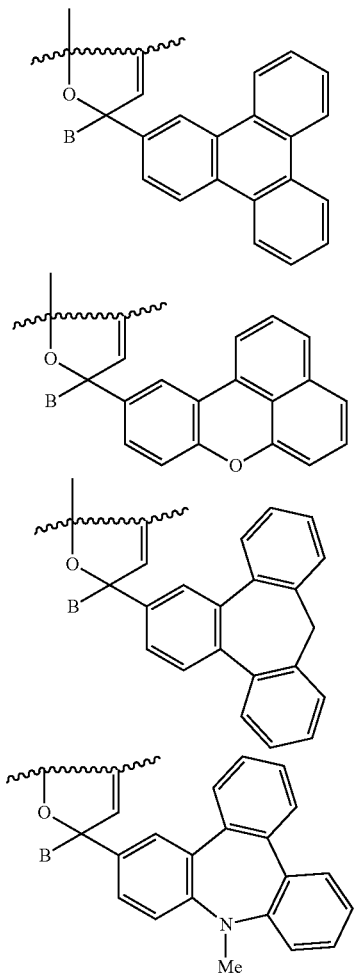

It will be appreciated, however, that also only one benzo ring may be present, fused via two adjacent carbon atoms of this V—(CR$_8$R$_9$)$_p$—W moiety.

As already observed, the compounds of the invention, relative to the photochromic 2H-naphtho[1,2-b]pyrans known in the prior art (U.S. Pat. No. 5,645,767), which have no dibenzo[b,d]pyrano fusion, surprisingly exhibit a second strong absorption band of the open form in the visible wavelength range (see FIG. 2). Consequently, the formation of this second absorption band in the case of the compounds of the invention is unexpected.

To measure the spectral properties of the compounds of the invention, 350 ppm of the photochromic dye in each case were dissolved in an acrylate monomer matrix and subjected to thermal polymerization, following addition of a polymerization initiator, with the aid of a temperature program. The transmission properties in the excited state of the plastics glasses produced accordingly (2 mm thickness) were measured subsequently in accordance with DIN EN ISO 8980-3.

Figure 2:
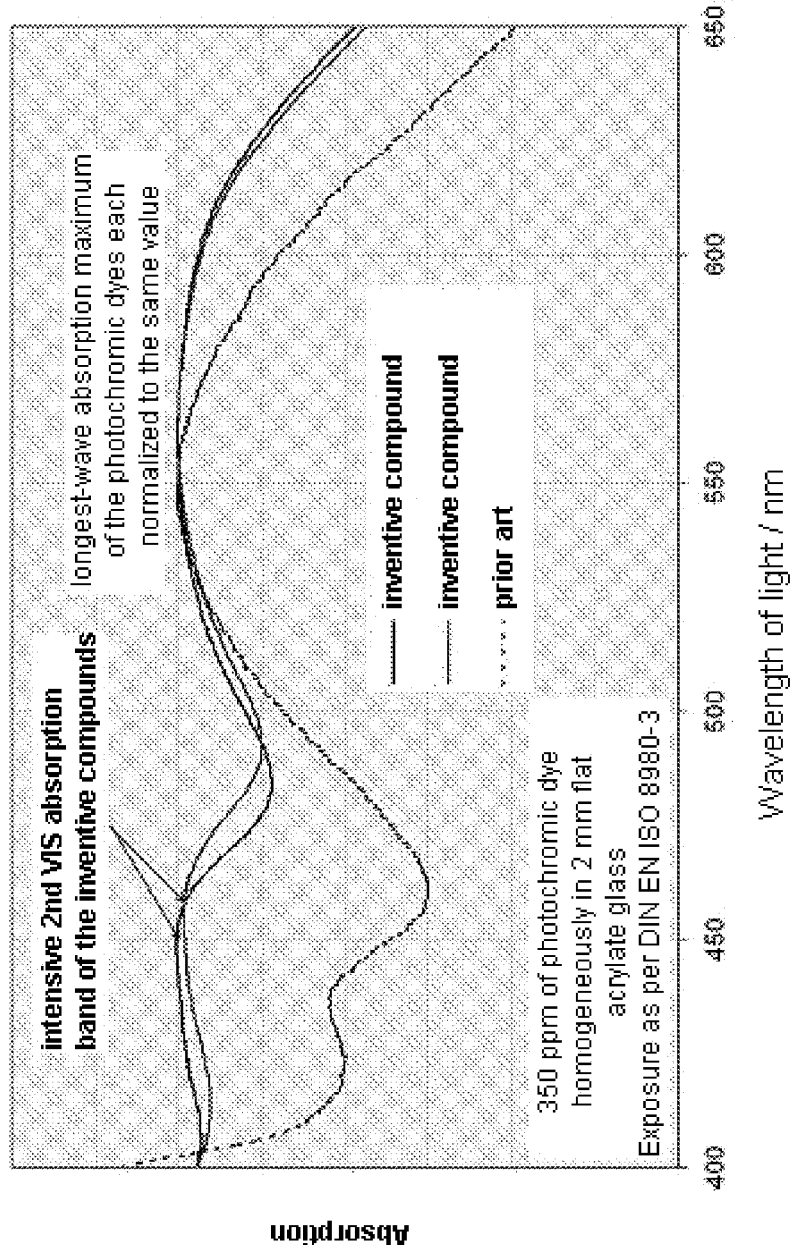
FIG. 2 shows the UV absorption spectra of specific inventive compounds in comparison to the prior art.

The structures of the compounds used and investigated in FIG. 2 are evident from the table below:

TABLE 1

Tabular comparison of the longest-wave absorption maxima in the excited state (An = anisyl, i.e., the 4-methoxyphenyl radical)

unexcited (colorless)

excited (colored)

| | B' | λmax (1) | λmax (2) | Apparent color |
|---|---|---|---|---|
| Prior art from U.S. Pat. No. 5,645,767 (without the inventive dibenzo [b,d]pyrano fusion) | anisyl | — | 550 nm | violet |
| Inventive compound 1 | anisyl | 450 nm | 560 nm | (reddish) gray |
| Inventive compound 2 | 6-methoxy-2-naphthyl | 455 nm | 565 nm | (brownish) gray |

FIG. 2 shows the UV absorption spectra of inventive compounds 1 and 2 in comparison to the prior art. The formation of a double absorption band in the case of the inventive compounds in contrast to the prior art clearly shows the influence of the dibenzo[b,d]pyrano fusion on the absorption spectrum—for a molecular structure which is otherwise the same (see FIG. 2).

The present invention provides a class of new photochromic double absorption dyes which includes—according to the choice of substituents R$_1$ and R$_2$—not only compounds featuring extremely deep darkening and a slow lightening rate (for phototropic outdoor products and relatively high temperatures) but also compounds with a quicker lightening rate (for phototropic everyday glasses).

For the synthesis of the inventive compounds, suitably substituted methylidenesuccinic anhydrides are subjected in a first step to a Friedel-Crafts reaction with suitably substituted dibenzo[b,d]pyrano derivatives (step (i)). The —COOH group of the resultant intermediate is subsequently protected and this intermediate is subjected to a Michael addition with correspondingly substituted aryl-Grignard compounds (step (ii)). Following removal of the protecting group on the carboxyl, correspondingly substituted derivatives are formed via intramolecular cyclization by means of phosphoric acid (step (iii)). These substituted derivatives are subsequently reacted with suitably substituted 2-propyn-1-ol derivatives in accordance with step (iv) to give the inventive compounds. The synthesis scheme above is reproduced in FIG. 1. For preparing inventive compounds having the formula (II), the corresponding structurally isomeric dibenzopyrano derivatives are used in the course of the Friedel-Crafts reaction.

The compounds of the invention can be used in plastics materials or plastics articles of any kind and form for a multiplicity of end uses for which photochromic behavior is important. It is possible here to use one dye according to the present invention, or a mixture of such dyes. By way of example, the inventive photochromic fluorenopyran dyes can be used in lenses, more particularly ophthalmic lenses, lenses for eyewear of all kinds, such as ski goggles, sunglasses, motorcycle goggles, visors of crash helmets, and the like. Furthermore, for example, the inventive photochromic fluorenopyrans with defined dibenzo[b,d]pyrano fusion may also be used as sun protection in vehicles and living spaces, in the form of windows, protective screens, covers, roofs or the like.

For the production of photochromic articles of these kinds, the inventive photochromic fluorenopyrans with defined dibenzo[b,d]pyrano fusion may be applied to or embedded in a polymer material, such as an organic plastics material, by various methods described in the prior art, as already indicated in WO 99/15518.

A distinction is drawn here between bulk coloring and surface coloring methods. A bulk coloring method comprises, for example, the dissolution or dispersion of the photochromic compound or compounds in accordance with the present invention in a plastics material, by the addition of the photochromic compound(s) to a monomeric material prior to polymerization, for example. Another option for producing a photochromic article is the penetration of the plastics material or materials with the photochromic compound(s) by immersion of the plastics material into a hot solution of the photochromic dye or dyes in accordance with the present invention, or else a thermal transfer method, for example. The photochromic compound(s) may also, for example, be provided in the form of a separate layer between adjacent layers of the plastics material, as part of a polymeric film, for example. Also possible, furthermore, is the application of the photochromic compound(s) as part of a coating present on the surface of the plastics material. The expression "penetration" in this context is intended to mean the migration of the photochromic compound(s) into the plastics material, by means, for example, of the solvent-supported transfer of the photochromic compound(s) into a polymer matrix, vapor phase transfer, or other such surface diffusion processes. Advantageously it is possible for such photochromic articles, such as eyewear lenses, for example, to be produced not only by means of the customary bulk coloring, but also, in the same way, by means of surface coloring—in the case of the latter variant it is possible to achieve a surprisingly lower migration tendency. This is advantageous in particular in the case of subsequent finishing steps, since—for example, in the case of an antireflection coating, as a result of the lesser back-diffusion under reduced pressure—there are drastic reductions in instances of layer detachment and similar defects.

Overall, on the basis of the inventive photochromic fluorenopyrans with defined dibenzo[b,d]pyrano fusion, it is possible to apply or embed colorations, i.e., dyes, of any desired compatibility (compatible from a chemical point of view and in terms of color) to or in the plastics material, in order to satisfy not only esthetic considerations but also medical or fashion considerations. Accordingly, the dye or dyes specifically selected may vary as a function of the intended effects and requirements.

The invention claimed is:
1. Photochromic fluorenopyrans with defined dibenzo[b,d]pyrano fusion in accordance with the general formulae (I) or (II):

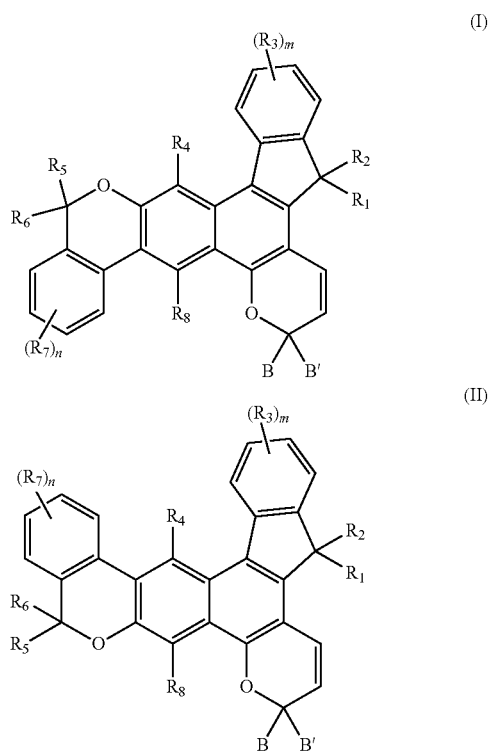

where for the radicals $R_1$, $R_2$, $R_3$, $R_4$, $R_5$, $R_6$, $R_7$, and $R_8$ are:
(i) each independently of one another are a substituent group α selected from a hydrogen atom, a $(C_1-C_6)$-alkyl radical, a $(C_1-C_6)$-thioalkyl radical, a $(C_3-C_7)$-cycloalkyl radical, which optionally contain one or more heteroatoms chosen from O or S, a $(C_1-C_6)$-alkoxy radical, a hydroxyl group, a trifluoromethyl group, bromine, chlorine, fluorine, and an unsubstituted or mono- or disubstituted phenyl, phenoxy, benzyl, benzyloxy, naphthyl, or naphthoxy radical, the substituents of the mono- or disubstituted phenyl, phenoxy, benzyl, benzyloxy, naphthyl, or naphthoxy radical are chosen from $(C_1-C_6)$-alkyl, $(C_1-C_6)$-alkoxy, bromine, chlorine, or fluorine; or
(ii)
(a) the radicals $R_1$ and $R_2$ together with the carbon atom bonded to the $R_1$ and $R_2$ radicals form a 3- to 8-membered, carbocyclic or heterocyclic ring which optionally (1) carries one or more-substituents chosen from the group α, or (2) has one to three aromatic or heteroaromatic ring systems fused thereto, the one to three aromatic or heteroaromatic ring systems being selected independently of one another from group β consisting of benzene, naphthalene, phenanthrene, pyridine, quinoline, furan, thiophene, pyrrole, benzofuran, benzothiophene, indole, and carbazole, which may be substituted in turn by one or more substituents selected from group α, and, if two of the α substituents carried on the 3- to 8-membered carbocyclic or heterocyclic ring formed by the $R_1$ and $R_2$ radicals are located on the same ring carbon atom, they may in turn form a 3- to 8-membered carbocyclic or heterocyclic ring, and/or (b) the radicals $R_5$ and $R_6$, together with the carbon atom bonded to the $R_5$ and $R_6$ radicals, form a 3- to 8-membered carbocyclic or heterocyclic ring which optionally (1) carries one or more-substituents chosen from the group α, or (2) has one to three aromatic or heteroaromatic ring systems fused thereto, the one to three aromatic or heteroaromatic ring systems being selected independently of one another from group β consisting of benzene, naphthalene, phenanthrene, pyridine, quinoline, furan, thiophene, pyrrole, benzofuran, benzothiophene, indole, and carbazole, which may be substituted in turn by one or more substituents selected from group α, and, if two of the α substituents carried on the 3- to 8-membered carbocyclic or heterocyclic ring formed by the $R_5$ and $R_6$ radicals are located on the same ring carbon atom, they may in turn form a 3- to 8-membered carbocyclic or heterocyclic ring, and/or (c) two adjacent radicals $R_3$ form a fused benzene ring, which may be unsubstituted or mono- or disubstituted, in which case the substituents may be selected in turn from group α; and/or (d) two adjacent radicals $R_7$ form a fused benzene ring, which may be unsubstituted or mono- or disubstituted, in which case the substituents may be selected in turn from group α; and when any of (iia-iid) are present, the remaining $R_1$, $R_2$, $R_3$, $R_4$, $R_5$, $R_6$, $R_7$, or $R_8$ groups are independently chosen from α;

m and n independently of one another are an integer from 1 to 4, and B and B' independently of one another are selected from one of the following groups a) or b), where a) are mono-, di-, and trisubstituted aryl radicals, where the aryl radical is selected from phenyl, naphthyl, or phenanthryl;

b) are unsubstituted, mono- and disubstituted heteroaryl radicals, the heteroaryl radical being selected from pyridyl, furanyl, benzofuranyl, thienyl, benzothienyl, 1,2,3,4-tetrahydrocarbazolyl or julolidinyl, the substituents of the aryl or heteroaryl radicals in a) and b) being substituents selected from the group:

(i) α, (ii) group χ consisting of amino, mono-($C_1$-$C_6$)-alkylamino, di-($C_1$-$C_6$)-alkylamino, mono- and diphenylamino unsubstituted or mono- or disubstituted on the phenyl ring, piperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, unsubstituted or mono- or disubstituted phenothiazinyl, unsubstituted or mono- or disubstituted phenoxazinyl, unsubstituted or mono- or disubstituted 1,2,3,4-tetrahydroquinolinyl, unsubstituted or mono- or disubstituted 2,3-dihydro-1,4-benzoxazinyl, unsubstituted or mono- or disubstituted 1,2,3,4-tetrahydroisoquinolinyl, unsubstituted or mono- or disubstituted phenazinyl, unsubstituted or mono- or disubstituted carbazolyl, unsubstituted or mono- or disubstituted 1,2,3,4-tetrahydrocarbazolyl and unsubstituted or mono- or disubstituted 10,11-dihydrodibenzo[b,f]azepinyl, the substituent or substituents of the mono- or disubstituted groups in the group α or group χ being independently selected from ($C_1$-$C_6$)-alkyl, ($C_1$-$C_6$)-alkoxy, bromine, chlorine, or fluorine; or (iii) where two directly adjacent substituents of the aryl or heteroaryl radicals in a) and b) are a V—$(CR_8R_9)_p$—W moiety, where p is 1, 2 or 3, the radicals $R_8$ and $R_9$ each independently of one another are a substituent selected from group α, and V and W independently of one another may be —O—, —S—, —N($C_1$-$C_6$)alkyl)-, —N($C_6H_5$)—, —CH$_2$—, —C(CH$_3$)$_2$—, or —C($C_6H_5$)$_2$—, optionally two or more adjacent $CR_8R_9$ units of this V—$(CR_8R_9)_p$—W moiety are part of a benzene ring fused thereto, optionally the benzene ring in each case contains in turn one or more substituents selected from group α, or V or W, together with the respectively adjacent $CR_8R_9$ unit, are a fused benzene ring, which may be unsubstituted or mono- or disubstituted, the substituents thereof are selected from group α.

2. The photochromic fluorenopyrans with defined dibenzo [b,d]pyrano fusion as claimed in claim 1, where the radicals $R_1$ and $R_2$ independently of one another are selected from a hydrogen atom, a ($C_1$-$C_6$)-alkyl radical, or a ($C_3$-$C_7$)-cycloalkyl radical.

3. The photochromic fluorenopyrans with defined dibenzo [b,d]pyrano fusion as claimed in claim 1, where $R_1$ and $R_2$, together with the carbon atom bonded to these radicals, form a 5- to 7-membered carbocyclic or heterocyclic ring which optionally carries one or more substituents from group α.

4. The photochromic fluorenopyrans with defined dibenzo [b,d]pyrano fusion as claimed in claim 1, where $R_5$ and $R_6$ independently of one another are selected from a hydrogen atom, a ($C_1$-$C_6$)-alkyl radical, or a ($C_3$-$C_7$)-cycloalkyl radical.

5. The photochromic fluorenopyrans with defined dibenzo [b,d]pyrano fusion as claimed in claim 1, which have the general formula (I).

6. The photochromic fluorenopyrans with defined dibenzo [b,d]pyrano fusion as claimed in claim 1, which have the general formula (III) below:

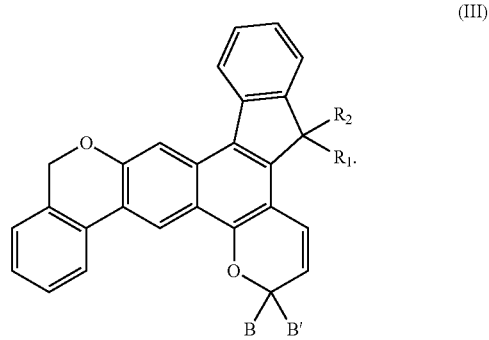

(III)

7. The photochromic fluorenopyrans with defined dibenzo [b,d]pyrano fusion as claimed in claim 1, where the radicals B and B' independently of one another are selected from the group a).

8. A plastic material comprising one or more of the photochromic fluorenopyrans with defined dibenzo[b,d] pyrano fusion as claimed in claim 1.

9. The plastic material of claim 8, wherein the plastic material is an ophthalmic lens.

\* \* \* \* \*